US005939357A

United States Patent [19]

Jones et al.

[11] Patent Number: 5,939,357

[45] Date of Patent: Aug. 17, 1999

[54] FUNGICIDE COMPOSITIONS

[75] Inventors: Keith A. Jones, Yardley, Pa.; Anthony E. Winston, East Brunswick, N.J.; M. Stephen Lajoie, Basking Ridge, N.J.; Amy L. Joseph, Hopewell, N.J.

[73] Assignee: Church & Dwight Co., Inc.

[21] Appl. No.: 08/071,963

[22] Filed: Jun. 7, 1993

Related U.S. Application Data

[62] Division of application No. 07/883,422, May 12, 1992, abandoned.

[51] Int. Cl.$^{6}$ .......................... A01N 55/02; A01N 55/04; A01N 59/00; A01N 59/16

[52] U.S. Cl. .......................... 504/101; 424/600; 424/617; 424/630; 424/637; 424/638; 424/650; 424/715; 424/716; 424/717; 71/DIG. 1; 514/53; 514/247; 514/386; 514/388; 514/395; 514/412; 514/433; 514/478; 514/479; 514/492; 514/493; 514/499

[58] Field of Search .......................... 514/493, 53, 247, 514/386, 388, 395, 412, 433, 478, 479, 492, 499, 500, 574, 617, 625, 724, 731, 734, 738, 764; 424/44, 421, 715, 716, 717, 600, 617, 630, 637, 638, 650; 504/101; 71/DIG. 1

[56] References Cited

U.S. PATENT DOCUMENTS

| | | | |
|---|---|---|---|
| 3,140,977 | 7/1964 | Duyfjes et al. | 514/493 |
| 4,599,233 | 7/1986 | Misato et al. | 424/717 |
| 5,004,614 | 4/1991 | Staniforth | 424/466 |
| 5,174,804 | 12/1992 | Rehberg et al. | 504/101 |

FOREIGN PATENT DOCUMENTS

| | | |
|---|---|---|
| 52-07438 | 1/1977 | Japan . |
| 53-96319 | 8/1978 | Japan . |
| 60-153785 | 8/1985 | Japan . |
| 61-10096 | 1/1986 | Japan . |

OTHER PUBLICATIONS

The Merck Index, 10th Ed., NJ, Merck & Co., Inc., 1983, pp. 818–819.

Van Nostrand Reinhold Encyclopedia of Chemistry, 4th Ed., NY, Van Nostrand Reinhold Company, 1984, p. 85.

*Primary Examiner*—John Pak
*Attorney, Agent, or Firm*—Irving Fishman

[57] ABSTRACT

This invention provides a novel fungicide composition which has a bicarbonate-containing inorganic salt ingredient which enhances the efficacy of a fungicide ingredient for the treatment of cultivated crops. An invention fungicide composition also contains a surfactant ingredient, and a water-soluble organic compound which functions as a compatibility enhancing ingredient in aqueous formulations, and the ingredients improve the spreadability and adhesiveness of the composition when applied to foliage. An invention fungicide composition also contains a fertilizer-effective ratio of nitrogen, phosphorus and potassium.

4 Claims, No Drawings

FUNGICIDE COMPOSITIONS

This application is a division, of application Ser. No. 07/883,422, filed May 12, 1992 now abandoned.

BACKGROUND OF THE INVENTION

Fungi are plants which obtain their nutrition from an organic carbon source. The body of the fungus secretes enzymes which degrade the organic substrate on which they are growing and yield smaller entities. These in turn are absorbed into the body of the fungus and are metabolized and provide energy to carry on vital processes.

The control of phytopathogenic fungi is of great economic importance since fungal growth on plants or on parts of plants inhibits production of foliage, fruit or seed, and the overall quality of a cultivated crop.

There is also a serious worldwide problem of mold growth in food materials, such as grains, animal feeds, animal feed ingredients, whole crop, and hay. This problem is most serious in tropical zones of both the eastern and western hemispheres, where sustained high humidities cause excessive moisture to be absorbed in such products.

One reason molds present such a serious problem is that they produce dangerous mycotoxins, some of which are carcinogenic. One of the common molds *Aspergillus flavus,* produces the mycotoxin aflatoxin which, in addition to other toxic characteristics, interferes with the immune system's ability to produce gamma globulin, the protein that is part of the immune system. The resulting breakdown of the immune system renders animals that have ingested such mold vulnerable to a variety of diseases.

Because of the vast economic ramifications of fungal propagation in agricultural and horticultural cultivations, a broad spectrum of fungicidal and fungistatic products have been developed for general and specific applications.

Of particular interest with respect to the present invention embodiments are fungicide compositions which contain one or more inorganic bicarbonate compounds. It is known that bicarbonate and carbonate compounds exhibit fungicidal properties for agricultural purposes.

Phytopathology, 48, 169 (1931) by R. H. Marloth describes studies involving the physiology of fungi. The reference reports studies which demonstrate that sodium and potassium bicarbonate and carbonate salts are toxic to fungi such as *Penicillum italicum* and *Penicillum digitalum.*

U.S. Pat. No. 1,560,558 discloses the use of one or more of lithium carbonate, sodium carbonate, sodium bicarbonate, potassium bicarbonate, potassium carbonate and ammonium bicarbonate as a fungicide.

Japanese patent 53090319 describes the application of potassium bicarbonate as an active biocide for the control of fungal diseases common to tomato and cucumber plants.

Japanese patent 53118523 describes the combination of sodium bicarbonate and lecithin as an active agent for the control of agricultural and fruit storage fungus diseases.

Japanese patent 56043207 describes a biocidal composition containing sodium bicarbonate and a polyglycerol fatty acid ester. The biocide controls *Penicillum digitatum* on oranges, *Sphaerotheca fuligenea* on cucumbers, *Piricularia oryzae* on rice, and mosaic virus on tomatoes.

Japanese patent 60097909 describes a soil fungicide prepared by admixing slaked lime with sodium bicarbonate, potassium bicarbonate, boric acid and phenolphthalein.

German patent DE 2927994 describes a fungicide which consists of sodium bicarbonate incorporated into a food-compatible surfactant such as saccharose laurate.

Japanese patent 57062208 describes horticultural fungicides in which the addition of sodium bicarbonate to polyoxin or thiophanatemethyl increases the fungicidal activity of the organic biocide against *Botrytis cinerea* on cucumbers.

Japanese patent 58023609 describes an agricultural fungicide composed of a mixture of sodium bicarbonate or potassium bicarbonate with cupric hydroxide, basic copper carbonate or basic copper sulfate. The combination of ingredients exhibits a synergistic fungicidal effect against cucumber early blight, tomato wilt, rice sheath blight, rice blast and citrus canker.

There remains a continuing need for the development of new and more effective fungicides which possess preventive, curative and systemic activity for the protection of cultivated plants, with a minimum of phytotoxic side effects.

Accordingly, it is an object of this invention to provide a biocide composition which is a blend of inorganic and organic compounds exhibiting fungicidal properties.

It is another object of this invention to provide a fungicide composition which is a dry blend of ingredients which include a bicarbonate salt which enhances the biocidal activity of a fungicide ingredient.

Other objects and advantages of the present invention shall become apparent from the accompanying description and examples.

DESCRIPTION OF THE INVENTION

One or more objects of the present invention are accomplished by the provision of a fungicide composition which is a dry blend formulation comprising (1) an ingredient selected from alkali metal and ammonium bicarbonates; (2) a compatibility enhancing ingredient selected from water-soluble organic compounds which are in solid form at a temperature below about 10° C.; and (3) a fungicide ingredient.

In another embodiment this invention provides an aqueous fungicidal formulation having a content comprising (1) an ingredient selected from alkali metal and ammonium bicarbonates; (2) a compatibility enhancing ingredient selected from water-soluble organic compounds which are in solid form at a temperature below about 10° C.; and (3) a fungicide ingredient.

The inorganic salt ingredient is selected from compounds which include sodium bicarbonate, potassium bicarbonate, lithium bicarbonate and ammonium bicarbonate. In a further embodiment, the inorganic salt ingredient can include an additional compound selected from sodium carbonate, potassium carbonate, lithium carbonate and ammonium carbonate.

The inorganic salt ingredient typically will comprise between about 10–80 weight percent, based on the weight of dry blend formulation.

Illustrative of inorganic salt ingredients in a formulation are sodium, potassium, lithium or ammonium bicarbonate, or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–12. Aqueous fungicidal formulations of the present invention tend to have a higher fungicidal activity at higher pH values.

A compatibility enhancing ingredient of the present invention fungicide compositions is a water-soluble organic compound which is in solid form at a temperature below about 10° C. Suitable compounds include acetamide, acetylurea, alanine, aminoquanidine, aminomalonate salt, aminopyridine, arabinose, benzenesulfonate salt, benzoate salt, citraconate salt, citrate salt, crotonate salt, cyclohexanol, dihydroxyacetone, dihydroxyacetone phosphate salt, dihydroxybenzene, dimethylurea, ethanolamine, ethyl alaninate, ethyl arsonate, ethylglycine, ethylurea, ethylenedisulfonate salt, ethyleneurea, paraformaldehyde, fucose, glutamate salt, glycerol, glycerol nitrate, glycerol phosphate guanidine, hexamine, mannitol, fructose, glucose, hydroxyurea, lactate salt, lactose, lysine, maleic amide, malonate salt, maltose, maltodextrin, methoxypyridine, methyl acetate, methyl carbamate, methyl ethyl sulfone, methyl glucoside, methylhydantoin, methylinositol, methylthiourea, methyluracil, methylurea, methylenedisulfonate salt, muconate salt, naphtholdisulfonate salt, nitrobenzoate salt, nitropentanediol, nitrophenol salt, nitrourethane, pentaglycerol, phenol, phenylenediamine, polydextrose, propionamide, propyl carbamate, propylurea, purine, pyrazine, pyrimidine, ribose, saccharate salt, sarcosinate salt, semicarbazide, sorbate salt, succinimide, sucrose, tartarate salt, tetrahydrobenzoate salt, tetrahydroquinoline, tetrazine, thiourea, threonine, triaminobenzene, triazole, triethylphosphine oxide, triethylenetetramine, trihydroxybenzene, trimethylurea, urea, xylenol, xylose, xylylene glycol, polyvinylpyrrolidone, sodium carboxymethylcellulose, xanthan gum, guar gum, locust bean gum, gum acacia, gum tragacanth, potassium alginate, potato agar, and the like.

The compatibility enhancing ingredient is incorporated in a quantity between about 0.5–20 weight percent, based on the weight of ingredients in a dry blend fungicide composition.

The term "water-soluble" as employed herein refers to a compatibility enhancing organic compound which has a solubility of at least about one gram per 100 grams of water at 25° C.

The fungicidal ingredient of an invention fungicide composition is included in a quantity which will provide a concentration between about 0.01–10 weight percent of the medium which is being applied to seeds, plants, trees, harvested crops, soil, and the like. The medium can be a dry blend dusting powder or an aqueous spraying formulation.

The fungicidal ingredient can be selected from a wide variety of organic and inorganic compounds or mixtures which are known and used in agriculture and horticulture applications, such as those listed in Agricultural Chemicals, Book IV, Fungicides, 1989 Revision (W. T. Thomson, Thomson Publications, Fresno, California 93791).

The general categories of fungicidal-active compounds include anilides, dithiocarbamates, halogenated derivatives, heterocyclic nitrogen derivatives, metallic derivatives, and the like.

Illustrative of fungicidal compounds are carbendazim, benomyl, thiophanate-methyl, thiabendazole, fuberidazole, dichlofluanid, cymoxanil, oxadixyl, metalaxyl, furalaxyl, benalaxyl, fenarimol, iprodione, procymidone, vinclozolin, penconazole, myclobutanil, pyrazophos, ethirimol, ditalimfos, tridermorph, triforine, nuarimol, triazbutyl, guazatine, propiconazole, prochloraz, flutriafol, chlortriafol, triadimefon, triadimenol, dichlobutrazol, fenpropimorph, fenpropidin, chlorozolinate, fenfuram, carboxin, oxycarboxin, methfuroxam, dodemorph, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bupirimate, etaconazole, cypofuram, biloxazol,dimethirimol, fenapanil, pyroxyfur, polyram, maneb, mancozeb, captafol, chlorothalonil, anilazine, thiram, captan, folpet, zineb, propineb, binapactryl, nitrothalisopropyl, dodine, dithianon, fentin hydroxide, fentin acetate, tecnazene, quintozene, dichloran, copper oxychloride, copper sulphate, Bordeaux mixture, and the like.

An invention fungicide composition can be applied directly to the foliage of plants, bushes and trees, or to the soil of a cultivated field, or to seeds prior to planting, or to paddy water and hydroponic culture systems. The fungicidal methods include preventive, protective, prophylactic and eradicant treatments.

Invention fungicide compositions can be in the form of dusting powders or granules, which optionally can include a solid diluent such as bentonite, calcium carbonate, magnesia, gypsum, kieselguhr, diatomaceous earth, and the like. Granules can be formed by impregnating pellets of filler with the fungicide composition ingredients, or by pelleting a dry blend fungicide composition in admixture with a powdered filler.

An invention fungicide composition also can be in the form of a dispersible powder in combination with a surfactant to facilitate dispersion of the powder in an aqueous medium. The surfactant is incorporated in a fungicide composition in a quantity between about 1–20 weight percent, based on the weight of water-insoluble ingredients.

The surfactant can be a cationic, anionic or nonionic type, or a mixture thereof. Suitable surfactants include cetyltrimethylammonium bromide; sodium lauryl sulfate; sodium dodecylbenzene-sulfonate; ammonium lignosulfonate; condensation products of ethylene oxide with fatty alcohols, amines or alkylphenols; partial esters of fatty acids and hexitol anhydrides; and the like.

An invention fungicide composition can be in the form of aqueous dispersions for use as dips, or as sprays for use in electrodynamic spraying techniques.

The ingredients in an invention fungicide composition can be selected to include nitrogen, phosphorus and potassium elements, in a ratio that allows the composition to function as a fertilizer in addition to its function as a fungicide, when applied to cultivated crops.

An invention fungicide composition can include one or more other biologically active ingredients, such as those which exhibit herbicidal, insecticidal or plant growth regulating activity.

A fungicide composition of the present invention has a novel combination of properties for the practice of pesticide control in agricultural and horticultural application.

The inorganic salt ingredient exhibits fungicidal properties, and the efficacy of the main fungicide ingredient is enhanced by the presence of the inorganic salt ingredient. A lesser quantity of fungicide ingredient then can be employed to achieve a desired degree of fungus control.

A present invention fungicide composition can be formulated to exhibit little or no phytotoxicity, or to minimize the toxic effects of salt stress on plants by the inorganic salt ingredient.

A significant feature of a present invention fungicide composition is the inclusion of a compatibility enhancing agent as an essential ingredient. Migration and settling of solid ingredients is minimized, and a dry blend formulation has a more uniformly distributed content because of the presence of the compatibility enhancing ingredient. An aqueous fungicide formulation has exceptional long term stability, without phase separation and precipitation of solids.

As a further advantage, a present invention aqueous fungicidal formulation has improved spreadability and adhesiveness when applied to plant foliage, and resists post-application fungicide drift. An applied formulation also exhibits humectant properties on coated foliage, and increased fungicidal efficacy because of the presence of the compatibility enhancing ingredient.

The following examples are further illustrative of the present invention. The components and specific ingredients are presented as being typical, and various modifications can be derived in view of the foregoing disclosure within the scope of the invention.

EXAMPLE I

This Example illustrates the preparation of a fungicide dusting powder in accordance with the present invention.

A blend of the following ingredients is prepared:

| | Parts |
|---|---|
| $KHCO_3$ | 30 |
| triphenyltin acetate | 5 |
| mannitol | 5 |
| talc | 65 |

The formulated blend is milled to provide a powder with a particle size of less than 0.5 micron.

EXAMPLE II

This Example illustrates the preparation of a copper-containing agricultural fungicide composition.

A blend of the following ingredients is prepared as a wettable powder formulation:

| | Parts |
|---|---|
| $NaHCO_3$ | 30 |
| basic copper sulfate | 5 |
| dihydroxybenzene | 2 |
| sodium lignosulfonate | 2 |
| kaolin | 30 |

The formulation is suspended in water (20% by weight solids), and is applied to plant foliage.

A synergistic fungicidal effect is observed when the aqueous formulation is applied to control cucumber damping-off, cucumber early blight, tomato wilt, and rice blast.

The formulation is applicable to seeds, soil and foliage.

Similar fungicidal activity is observed when an aqueous solution (10% by weight solids) containing dissolved $NH_4HCO_3$ (60 parts), $K_2Co_3$ (35 parts), basic copper sulfate (5 parts) and sodium benzenesulfonate (5 parts) is applied to plant foliage.

EXAMPLE III

This Example illustrates the preparation of a granulated fungicide composition which has a high suspension capacity in water.

A mixture of the following ingredients is prepared:

| | Parts |
|---|---|
| Chloridazon | 60 |
| $NH_4HCO_3$ | 10 |
| $KHCO_3$ | 5 |
| hexamine | 2 |
| sodium lignosulfonate | 20 |

The mixture is dispersed in water, and spray-dried at 180° C. The resulting granules have a 70% suspension capacity in water.

EXAMPLE IV

This Example illustrates the preparation of fungicide composition tablets which rapidly disintegrate and disperse in water.

| | Parts |
|---|---|
| Captan | 40 |
| $NaHCO_3$ | 35 |
| citric acid | 12 |
| Lomar PWA 10[(1)] | 10 |
| glyoxal | 2 |
| sodium lignosulfonate | 1 |

[(1)]sodium salt of alkylarylsulfonate condensation product (Jacques Wolf & Co.)

The ingredients are blended, and formed into tablets which disintegrate and disperse in water within about five minutes at 25° C.

EXAMPLE V

This Example illustrates the preparation of a water-dilutable liquid concentrate fungicide composition.

A liquid concentrate is prepared from the following ingredients:

| | Parts |
|---|---|
| Carboxin | 10 |
| $NaHCO_3$ (300 mesh) | 35 |
| $KHCO_3$ (300 mesh) | 35 |
| oleic acid monoglyceride | 30 |
| glyceryl monooctanoate | 10 |
| glycerol | 5 |

The ingredients are admixed and heated at 40° C. to form a concentrated liquid suspension. When the suspension is diluted with water, it forms a stable emulsion which has utility as a fungicide spray in agricultural applications.

EXAMPLE VI

This Example illustrates the preparation of an aqueous fungicidal formulation stabilized with a nonionic surfactant phosphate ester salt.

| | Parts |
|---|---|
| Benomyl | 22 |
| $KHCO_3$ | 10 |
| $NH_4CO_3$ | 10 |
| polyoxyethylene (7.6 mol)-phenylphenol ether phosphate diethanol-amine salt | 5 |
| sucrose | 5 |
| water | 50 |

The ingredients are added to the water medium with stirring to form a stable emulsion.

EXAMPLE VII

This Example illustrates the preparation of a fungicide composition suitable for treatment of seeds.

A fungicide composition is prepared by mixing and grinding the following ingredients:

| | Parts |
|---|---|
| pentachloronitrobenzene | 10 |
| sodium nitrophenol | 5 |
| $NH_4HCO_3$ | 20 |
| $K_2CO_3$ | 20 |
| mineral oil | 10 |
| china clay | 40 |

EXAMPLE VIII

This Example illustrates the preparation of a fungicide-fertilizer composition.

A blend of the following ingredients is prepared:

| | Parts |
|---|---|
| melamine | 40 |
| urea | 30 |
| potassium glycerol phosphate | 20 |
| Carboxin | 5 |
| $KHCO_3$ | 15 |

Granules are prepared by tumbling the blend, spraying added water to form tacky solids, and then drying the granulated product.

What is claimed is:

1. A fungicide composition which is a dry blend formulation comprising (1) between about 10–80 weight percent of an ingredient selected from the group consisting of alkali metal and ammonium bicarbonates, (2) between about 0.5–20 weight percent of a compatibility enhancing ingredient selected from the group consisting of water-soluble polyhydroxy compounds which are in solid form at a temperature below about 10° C., (3) between about 0.01–10 weight percent of a fungicide ingredient, and (4) between about 1–20 weight percent of a surfactant ingredient, based on the weight of water-insoluble ingredients; wherein the composition contains nitrogen, phosphorus and potassium elements in a ratio which is functional as a fertilizer formulation.

2. A fungicidal composition in accordance with claim 1 wherein the content of inorganic salt ingredient comprises potassium bicarbonate.

3. A fungicide composition in accordance with claim 1 wherein the content of inorganic salt ingredient comprises ammonium bicarbonate.

4. A fungicide composition in accordance with claim 1 wherein the content of inorganic salt ingredient comprises potassium bicarbonate and ammonium bicarbonate.

* * * * *